(12) United States Patent
Silberg

(10) Patent No.: US 11,197,987 B2
(45) Date of Patent: *Dec. 14, 2021

(54) ADMINISTRATION OF ANTIBIOTICS AND THERAPEUTIC AGENTS

(71) Applicant: Sonescence, Inc., Santa Rosa, CA (US)

(72) Inventor: Barry Neil Silberg, Santa Rosa, CA (US)

(*) Notice: Subject to any disclaimer, the term of this patent is extended or adjusted under 35 U.S.C. 154(b) by 88 days.

This patent is subject to a terminal disclaimer.

(21) Appl. No.: 14/297,110

(22) Filed: Jun. 5, 2014

(65) Prior Publication Data

US 2014/0288483 A1    Sep. 25, 2014

Related U.S. Application Data

(63) Continuation of application No. 13/205,097, filed on Aug. 8, 2011, now Pat. No. 8,747,384, which is a continuation of application No. 12/405,616, filed on Mar. 17, 2009, now abandoned.

(60) Provisional application No. 61/096,568, filed on Sep. 12, 2008.

(51) Int. Cl.
| | |
|---|---|
| *A61M 37/00* | (2006.01) |
| *A61K 31/546* | (2006.01) |
| *A61K 38/14* | (2006.01) |
| *A61B 17/3211* | (2006.01) |
| *A61N 7/00* | (2006.01) |
| *A61B 17/00* | (2006.01) |

(52) U.S. Cl.
CPC ..... *A61M 37/0092* (2013.01); *A61B 17/3211* (2013.01); *A61K 31/546* (2013.01); *A61K 38/14* (2013.01); *A61N 7/00* (2013.01); *A61B 2017/00889* (2013.01); *A61N 2007/0004* (2013.01); *A61N 2007/0017* (2013.01)

(58) Field of Classification Search
CPC . A61M 37/0092; A61K 38/14; A61K 31/546; A61B 17/3211
USPC ........................................................ 604/501
See application file for complete search history.

(56) References Cited

U.S. PATENT DOCUMENTS

| | | | |
|---|---|---|---|
| 3,630,198 | A | 12/1971 | Henkin |
| 4,190,495 | A | 2/1980 | Curtis, III |
| 4,368,203 | A | 1/1983 | Okamura et al. |
| 4,982,730 | A | 1/1991 | Lewis |
| 5,016,615 | A | 5/1991 | Driller et al. |
| 5,197,946 | A | 3/1993 | Tachibana |
| 5,399,723 | A | 3/1995 | Iinuma et al. |

(Continued)

FOREIGN PATENT DOCUMENTS

| | | |
|---|---|---|
| RU | 2119769 C1 | 10/1998 |
| RU | 2175565 C2 | 10/2001 |

(Continued)

OTHER PUBLICATIONS

As filed U.S. Appl. No. 14/725,694, filed May 29, 2015.

(Continued)

*Primary Examiner* — William R Carpenter

(57) ABSTRACT

Antibiotics are administered in a surgical site subcutaneously via a small or stab incision in the surgical field. Transcutaneous ultrasonic vibrations are applied across the surgical field, which is then opened in the usual manner, to thereby provide a surgical field which contains a vastly higher and more effective level of antibiotic. At the same time the underlying tissue is hydrated.

12 Claims, 6 Drawing Sheets

(56) References Cited

U.S. PATENT DOCUMENTS

| | | | |
|---|---|---|---|
| 5,559,108 A | 9/1996 | Kim et al. | |
| 5,578,572 A | 11/1996 | Horwitz et al. | |
| 5,580,575 A | 12/1996 | Unger et al. | |
| 5,884,631 A | 3/1999 | Silberg | |
| 5,980,512 A | 11/1999 | Silberg | |
| 6,018,678 A | 1/2000 | Mitragotri et al. | |
| 6,030,374 A | 2/2000 | McDaniel | |
| 6,039,048 A | 3/2000 | Silberg | |
| 6,041,253 A | 3/2000 | Kost et al. | |
| 6,074,657 A | 6/2000 | Brown | |
| 6,403,056 B1 | 6/2002 | Unger | |
| 6,428,491 B1 | 8/2002 | Weiss | |
| 6,464,680 B1 * | 10/2002 | Brisken | A61M 37/0092 604/501 |
| 6,484,052 B1 | 11/2002 | Visuri | |
| 6,565,521 B1 | 5/2003 | Silberg | |
| 6,569,099 B1 | 5/2003 | Babaev | |
| 6,623,444 B2 | 9/2003 | Babaev | |
| 7,025,735 B2 | 4/2006 | Soring | |
| 7,083,572 B2 | 8/2006 | Unger et al. | |
| 7,326,235 B2 | 2/2008 | Edwards | |
| 7,981,442 B2 | 7/2011 | Hood et al. | |
| 8,050,752 B2 | 11/2011 | Babaev | |
| 8,747,384 B2 | 6/2014 | Silberg | |
| 2002/0099356 A1 | 7/2002 | Unger et al. | |
| 2003/0092667 A1 | 5/2003 | Tachibana et al. | |
| 2004/0162546 A1 | 8/2004 | Liang et al. | |
| 2004/0220551 A1 | 11/2004 | Flaherty | |
| 2006/0222692 A1 | 10/2006 | Lane et al. | |
| 2006/0247601 A1 * | 11/2006 | Ellin | A61K 31/4164 604/500 |
| 2007/0167619 A1 | 7/2007 | Love et al. | |
| 2011/0301528 A1 | 12/2011 | Silberg | |
| 2012/0041309 A1 | 2/2012 | Coussios et al. | |
| 2012/0128776 A1 | 5/2012 | Chlon et al. | |
| 2012/0259222 A1 | 10/2012 | Coussios et al. | |
| 2012/0271169 A1 | 10/2012 | Coussios et al. | |
| 2013/0281916 A1 | 10/2013 | Wagstaffe et al. | |
| 2014/0276367 A1 | 9/2014 | Kersten et al. | |

FOREIGN PATENT DOCUMENTS

| | | |
|---|---|---|
| RU | 2218886 C2 | 12/2003 |
| RU | 2320381 C2 | 3/2008 |
| WO | 2015/059460 A1 | 4/2015 |
| WO | 2015/075442 A2 | 5/2015 |

OTHER PUBLICATIONS

As filed U.S. Appl. No. 14/725,734, filed May 29, 2015.
As filed U.S. Appl. No. 14/738,606, filed Jun. 12, 2015.
Barua et al,. "Convection-Enhanced Drug Delivery to the Brain Therapeutic Potential and Neuropathological Considerations," Brain Pathology (2014) 24:117-127.
Braizler, Dale W., et al., "Use of Antimicrobial Prophylaxis for Major Surgery: Baseline Results From the National Surgical Infection Prevention Project", Arch Surg., (Feb. 2005), vol. 140, pp. 174-182.
Byl, Nancy, "The Use of Ultrasound as an Enhancer for Transcutaneous Drug Delivery: Phonophoresis", Pharmacology Series, Physical Therapy (Jun. 1995), vol. 75, No. 6, 15 pages.
Champoux, N. et al., "Single-dose pharmacokinetics of ampicillin and tobramycin administered by hypodermoclysis in young and older healthy volunteers", Br J Clin Pharmacol, (1996), 42:325-331.
Dudley, Michael N., et al., "Comparative Penetration of Cefonicid and Cefazolin into the Atrial Appendage and Pericardial Fluid of Patients Undergoing Open-Heart Surgery", Antimicrobial Agents and Chemotherapy, (Sep. 1984), vol. 26, No. 3, p. 347-350.
Dyson, M. et al., "Stimulation of healing of varicose ulcers by ultrasound", Ultrasonics (Sep. 1976), pp. 232-236.
Forsberg et al., "Subharmonic imaging of contrast agents," *Ultrasonics*, (2000) 38:93-98.
Frisoli, Jr., A. et al., "Subcutaneous Hydration by Hypodermoclysis: A Practical and Low Cost Treatment for Elderly Patients", Drugs & Aging, (Apr. 2000), 16 (4): 313-319.
Frohly et al., "Ultrasonic cavitation monitoring by acoustic noise power measurement," *The Journal of the Acoustical Society of America*, (2012) 108(5).
Hockham et al., "A Real-Time Controller for Sustaining Thermally Relevant Acoustic Cavitation During Ultrasound Therapy," IEEE Transactions on Ultrasonics, Ferroelectrics, and Frequency Control, (Dec. 2010) 57(12):2685-2694.
Hompland et al., "Interstitial Fluid Pressure and Associated Lymph Node Metastasis Revealed in Tumors by Dynamic Contrast-Enhanced MRI," *Cancer Research*, (2012) 72(19):4899-4908.
Mangram, Alcicia J., et al., "Guideline for Prevention of Surgical Site Infection, 1999", Infection Control and Hospital Epidemiology, (Apr. 1999), vol. 20, No. 4, pp. 247-278.
Newman, M. K. et al., "Effects of Ultrasound Alonf and Combined with Hydrocortisone Injections by Needle or Hypospray", Presented as part of the Scientific pgrgram of the International Conference of Ultrasonics in Medicine, sponsored by the American Institute of Ultrasonics in Medicine, Los Angles, CA, (Sep. 6-7, 1957), pp. 206-209.
Ohge et al., "An Additional Dose of Cefazolin for Intraoperative Prophylaxis" Jpn J Surg (1999) 29:1233-1236.
Tranquart et al., "Clinical Use of Ultrasound Tissue Harmonic Imaging," *Ultrasound in Med. & Biol.*, (1999) 25(6):889-894.
Tsukamoto, Akira, et al., "1-MHz ultrasound enhances internal diffusivity in agarose gels", Applied Acoustics (2013) 74:1117-1121.
Foulds et al., "Pharmacokinetics of Sulbactam in Humans", *Antimicrobial Agents and Chemotherapy*, vol. 25 No 5, p. 692-699 (May 1983).
Kernodle et al., "Association of Borderline Oxacillin-Suceptible Strains of *Staphylococcus aureus* with Surgical Wound Infections", *Journal of Clinical Microbiology*, vol. 36 No. 1, p. 219-222 (Jan. 1998).
Lavery et al., "Validation of the Infectious Diseases Society of America's Diabetic Foot Infection Classification System", Clinical Infectious Diseases, vol. 44, pp. 562-565 (2007).
Turos et al., "Penicillin-bound polyacrylate nanoparticles: Restoringn the activity of B-lactam antibiotics against MRSA", *Bioorganic & Medicinal Chemistry Letters*, (17(12)), Jun. 15, 2007; pp. 3468-3472.
Wiggins et al., "Concentration of antibiotics in normal bone after intravenous injection", *The Journal of Bone and Joint Surgery*, 60, p. 90-96 (1978).
File History of U.S. Appl. No. 12/405,616, filed Mar. 17, 2009.
File History of U.S. Appl. No. 13/205,097, filed Aug. 8, 2011.
File History of U.S. Appl. No. 13/374,221, filed Dec. 15, 2011.

\* cited by examiner

ADMINISTRATION OF ANTIBIOTICS AND THERAPEUTIC AGENTS

CROSS-REFERENCE TO RELATED APPLICATIONS

The present application claims priority under 35 U.S.C. § 120 as a continuation of U.S. patent application Ser. No. 13/205,097, filed Aug. 8, 2011, which claims priority under 35 U.S.C. § 120 as a continuation of U.S. patent application Ser. No. 12/405,616, filed Mar. 17, 2009, which claims priority under 35 U.S.C. § 119(e) to U.S. Provisional Application No. 61/096,568, filed on Sep. 12, 2008. All of the aforementioned priority applications are herein expressly incorporated by reference in their entirety.

BACKGROUND OF THE INVENTION

The present invention relates to a method of administering antibiotics and related compounds to prevent infection at an open surgical site.

Prior methods of preventing surgical infection general involve administering either oral, but preferably intravenous doses of antibiotic prior to surgery to provide a systemic dispersion of antibiotic.

However, some patients experience side effects from systemic doses of antibiotics, such as subsequent GI distress due to a change in bacterial flora.

Moreover, a relatively high dose is required to provide enough antibiotics in the region of exposed tissue that is most susceptible to infection.

In U.S. Pat. No. 6,565,521 (issued to Silberg on May 20, 2003) discloses a method and system for removing body vessels from a patient for subsequent use in a grafting procedure, such as, for example, saphenous vein graft harvesting for a coronary bypass surgical operation. A quantity of a solution is infused into tissue surrounding the portion of the vessel to be removed. An external device is used to apply an energy field to the tissue to loosen the intercellular connections between the tissue and the vessel to be removed. One such device is an ultrasonic instrument having an ultrasonic transducer comprised of a composite of ultrasonic crystal transducers. Once the energy field has been applied, the portion of the vessel to be removed is separated from surrounding tissue and tributary vessels are ligated. The portion of the vessel is then transected and removed from the body.

U.S. Pat. No. 6,039,048 (issued to Silberg on Mar. 21, 2000) discloses that antibiotics may be injected with normal saline solution when ultrasonic energy is used to loosen fat tissue prior to removal by liposuction. The ultrasonic energy, which is transmitted via the saline solution, disrupts connective tissue between fat cells and hence facilitates the removal of the fatty tissue.

However, as the fat cells are removed from the area with the liposuction tube, and no further surgical incisions are made, it is expected that antibiotics are removed with the fat tissue and will not provide a longer term therapeutic effect.

Accordingly, there is an on-going need for an improved means to administer antibiotic compounds prior to surgery so as to minimize infection.

It is therefore a first object of the present invention to provide a more effective means for the targeted delivery of antibiotics or other therapeutic agents prior to surgery.

It is an additional objective of the invention to pre-operatively deliver such antibiotics or therapeutic agents and avoid potential complications and secondary effects of systemic application.

It is a further object of the invention to provide a higher local concentration of antibiotic in the surgical site which will be open and hence subject to infection, and thus achieve a lower incidence of infection, as well as the faster healing of patients.

It is still another object of the invention to provide a means to reduce the quantity of antibiotics used pre- and post-operatively.

It is another object of the invention to also minimize the dehydration of tissues that are exposed during surgery.

SUMMARY OF THE INVENTION

In the present invention, the above and other objects are achieved by providing a process for protecting a surgical site from infection, the process comprising the steps of defining within a surgical or treatment field an incision line, making a first small incision at or about the incision line, injecting a quantity of antibiotic or other therapeutic agent subcutaneously about the incision line via the first small incision, broadcasting ultrasonic energy transcutaneously to disperse the antibiotic agent and fluid subcutaneously, making a second incision along the incision line, the first incision being a fraction of the incision line, but generally no more than 2 mm, and the second incision being along substantially all or the remainder of the incision line.

The above and other objects, effects, features, and advantages of the present invention will become more apparent from the following description of the embodiments thereof taken in conjunction with the accompanying drawings.

DETAILED DESCRIPTION OF THE PREFERRED EMBODIMENT

Figure 1:
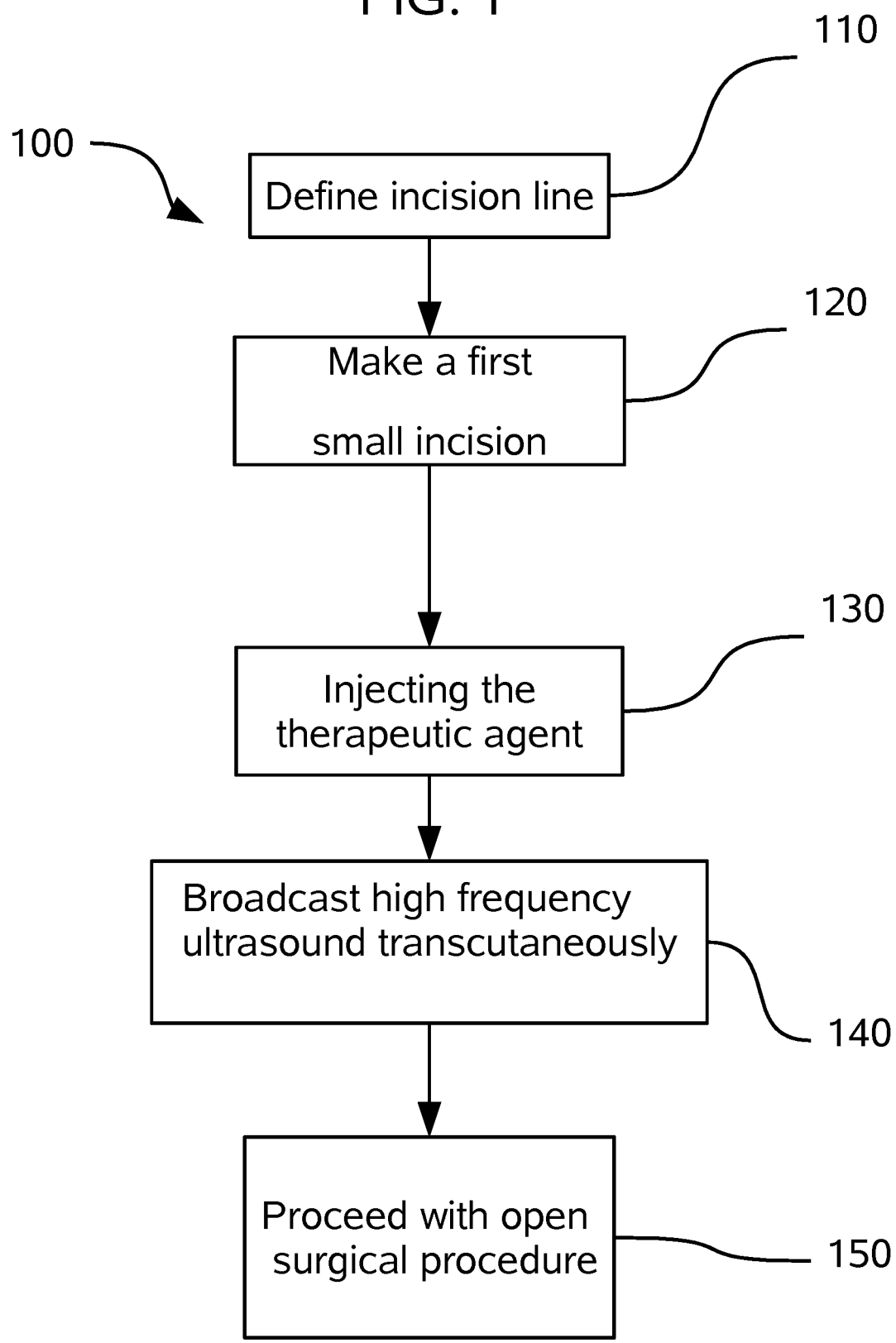
FIG. 1 is a flow chart of the method.

Referring to FIGS. 1 through 6, wherein like reference numerals refer to like components in the various views, there is illustrated therein a new and improved method for the pre-surgical prophylactic administration of antibiotics and other therapeutic agents, generally denominated 100 herein.

In accordance with the present invention, antibiotics or another therapeutic agents is injected subcutaneously via a small or stab incision using a blunt cannula into the area to be treated. High frequency ultrasound energy is broadcast transcutaneously to disperse the antibiotic or other therapeutic agent into the subcutaneous volume to be exposed in surgery by a process of ultrasonic micro streaming. If the area is to be opened, as in surgery, the addition of fluid together with the antibiotic or other therapeutic agent adds extra hydration to the treated area, thus preventing dehydration from exposure during surgery.

Accordingly, the process is carried out by first defining a surgical or treatment field and the incision line or region 201 thereof. In the first step 110 in the process 100, as described in the Flow chart of FIG. 1, the incision line 201 is a reference line, typically drawn on the patient's skin 216 that defines the entire length of the eventual surgical incision. However, as will be more fully understood in light of the further disclose of the method, the incision line 201 could also represent the region of the body tissue to be exposed during surgery or otherwise most subject to post operative surgical infection.

Figure 2:
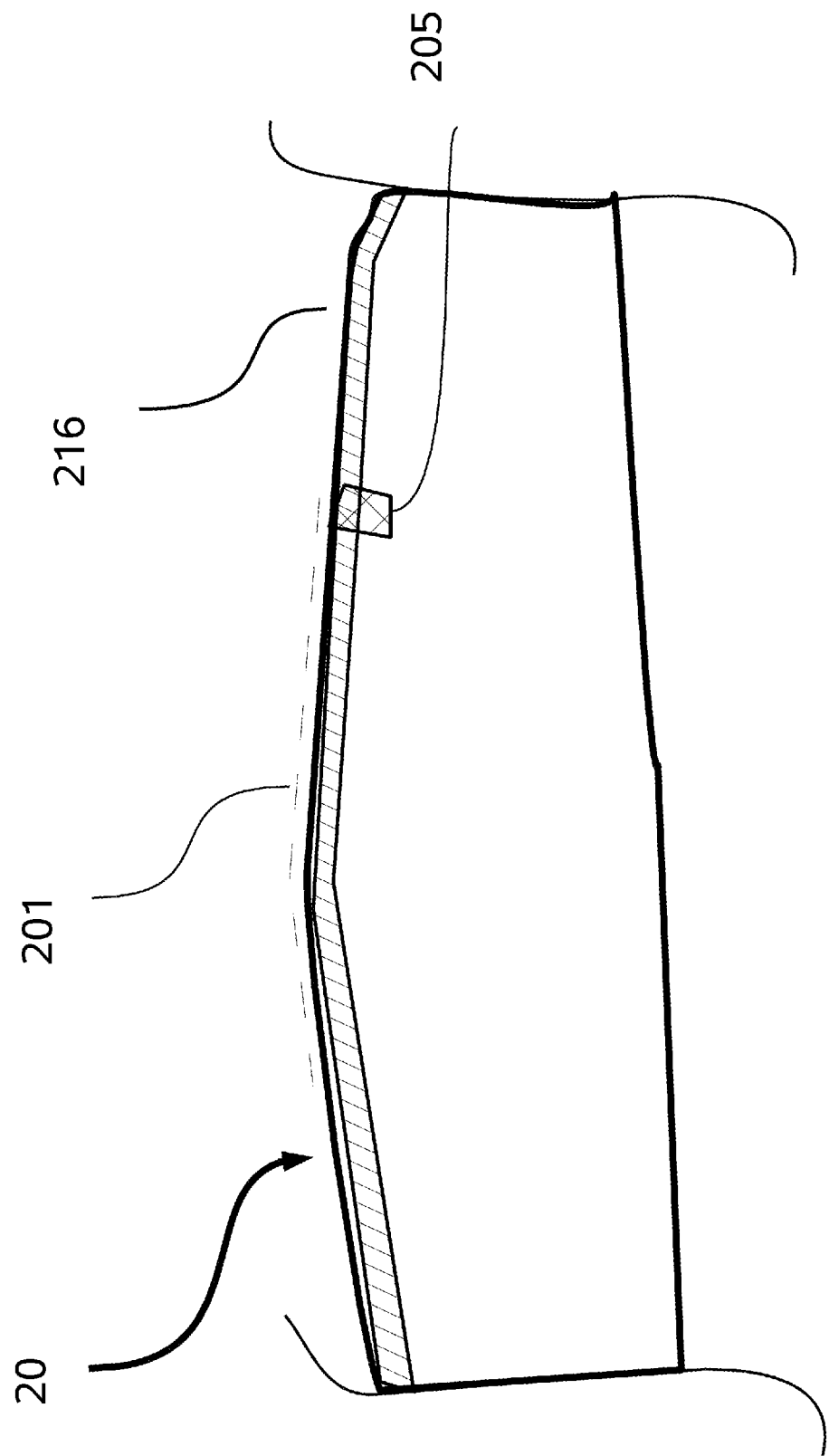
FIG. 2 is a schematic section of a patient showing the first step in the method.

Referring to FIG. 2, a portion of the patient's body 20 in which a surgical procedure is to be performed is shown in section. In the next step 120 in the process 100, as a short stab wound 205 is made at the end of the intended surgical incision line 201.

Figure 3:
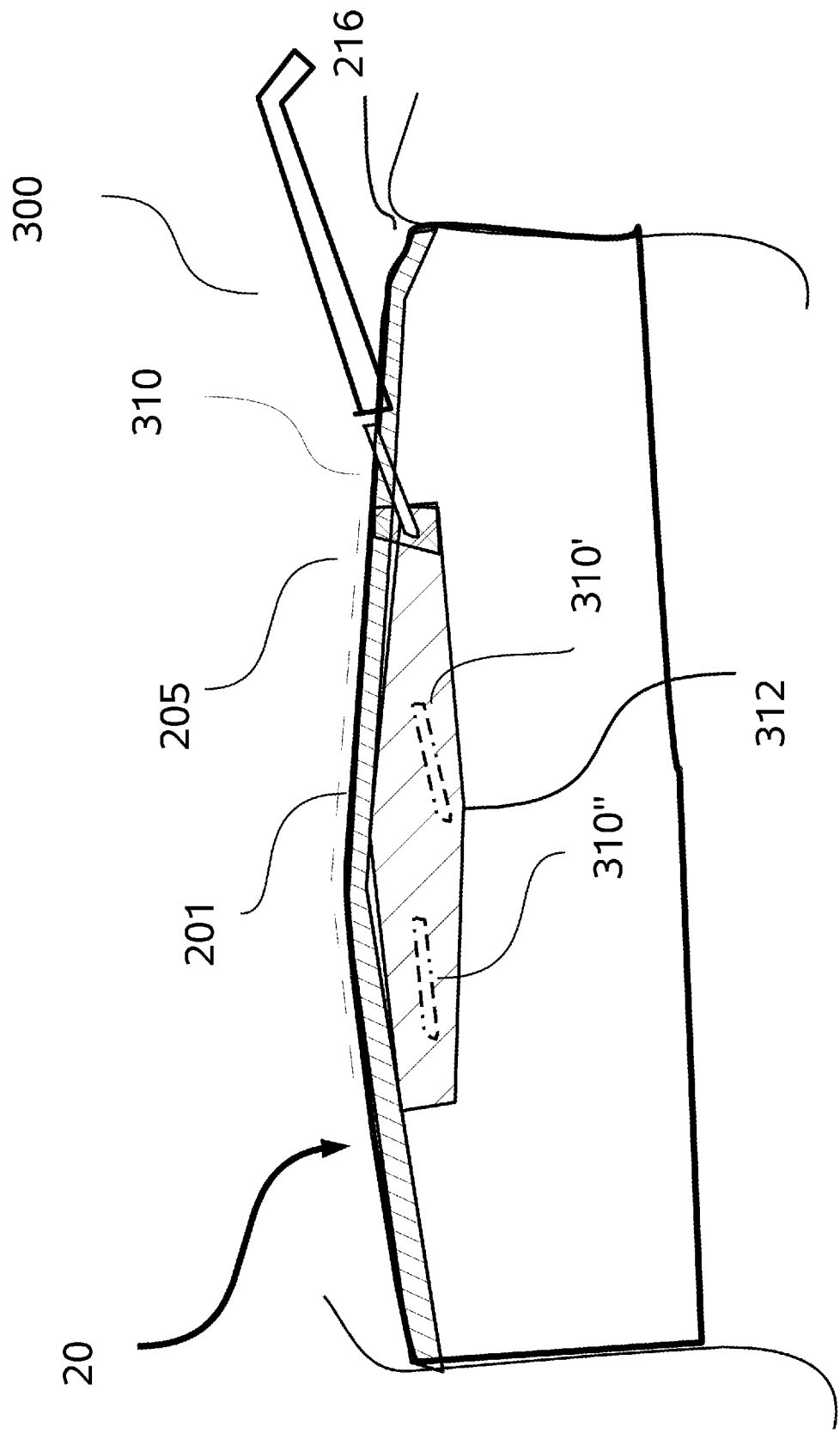
FIG. 3 is a schematic section of a patient showing the second step in the method.

In the next step 130 in the process 100, as shown in FIG. 3, an irrigating cannula 300 comprising a hollow blunt tip 310 is inserted into the short stab wound 205. A solution of fluid containing an antibiotic or related therapeutic agent is delivered through the hollow needle tip 310 of the infusion cannula 300 and is infused into a volume 312 of the tissue underlying the surgical incision line 201, which will eventually be exposed in the surgical procedure. As this incision 205 is small the potential for infection through it, while antibiotics are being delivered, is comparatively small.

The volume 312 of tissue to be infused is determined by the surgical procedure. In general, the volume 312 of infusion should include the area surrounding the portion of the tissue that will be exposed and is subject to infection as well as dehydration. Suitable isotonic solutions for dissolving an antibiotic agent may be used for infusion, for example, saline or ringer's lactate, with the optional addition of epinephrine or xylocaine. The amount of solution may vary depending upon the size of the patient and the area to be infused. Varying degrees of solution infusion are possible while keeping in mind that the infused solution attenuates the ultrasonic energy heating to protect the tissue and provides a greater hydration effect. The fluid is preferably warmed to body temperature and is infused in the subcutaneous tissue.

As shown by the outline of the needle 310' and 310", the cannula 300 is moved externally such that tip of the needle 330 is transport across region 312 dispersing the therapeutic agent therein. Typically the cannula tip 310 is moved under the incision line at a rate commensurate with the fluid injection rate to provide an even and uniform does of the agent in the surgical area. It should be noted that region 312 is generally at least a substantial portion of the tissue below the intended surgical incision line 201. Thus, the depth of the short or stab wound 205 as well as that of region 312 can be just under the skin 216 or deeper, but is generally about 1 cm or less, depending in part on the location of the organ or anatomy requiring surgery, as well as the potential infusion kinetics of the antibiotic agent in the surrounding tissue, as will be further described.

Figure 4:
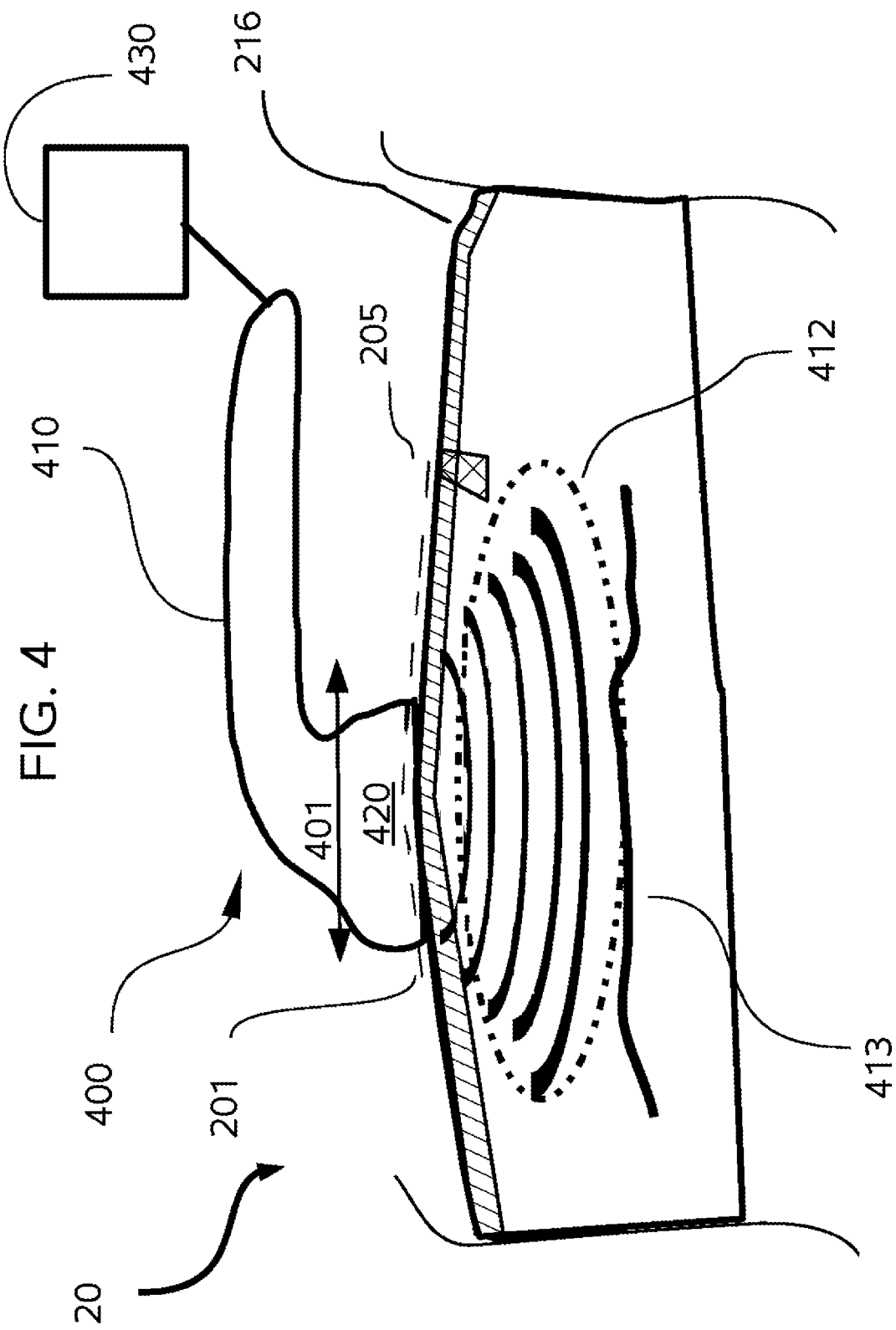
FIG. 4 is a schematic section of a patient showing the third step in the method

As illustrated in FIG. 4, in process step 140, after the therapeutic solution is infused in step 130, and removal of the cannula 300 through the first incision 205, the physician externally applies ultrasound through the skin over the incision or treatment line region. The ultrasonic instrument 400 comprises a handle 410 coupled to a power source 430, and an ultrasonic transducer head 420 (protected by a sterile sheath) is used to apply ultrasonic energy though the skin 216 of the patient to the volume 312 of tissue which has received the antibiotic agent. Preferably the ultrasonic transducer in head 420 or elsewhere comprises crystals embedded in a polymer, such as, for example, a lead zirconate titanate crystals embedded in acrylate, that diffuses the energy relatively more superficially than other transducers. A transmitting gel is applied to the skin 216 to provide coupling between the ultrasonic transducer head 420 and the patient's skin 216 for the efficient transmission of the ultrasonic waves. The physician holds the instrument 430 by the handle 431 and applies the transducer head 432 to the patient's skin 216, moving the transducer generally over the intended surgical incision line 201 (as in the direction of arrow 401) but most generally throughout the area of skin corresponding to the volume 412 of tissue beneath the skin 216 to be treated. This volume of tissue 412 (as shown in FIG. 5) generally extends down to the deep fascia 413.

In one embodiment, the ultrasonic field is introduced into the tissue through the skin at a frequency of 1 MHz and a power density of 3 watts/cm2 for a sufficient time for the tissues to become warm and soft generally about 2-5 minutes. Preferably an ultrasonic frequency of about 0.5 to 5 MHz is used with a power density ranging from about 2.5 to 4 watts/cm2. The application of the ultrasonic energy is believed to cause cavitation and micro streaming, i.e., the movement of the fluid in a linear direction away from the ultrasonic energy source. Preferably, the temperature of the site is monitored to prevent excess heat buildup. Should the ultrasonic vibration cause too much heat, the surrounding tissue and skin can be inadvertently damaged.

Figure 5:
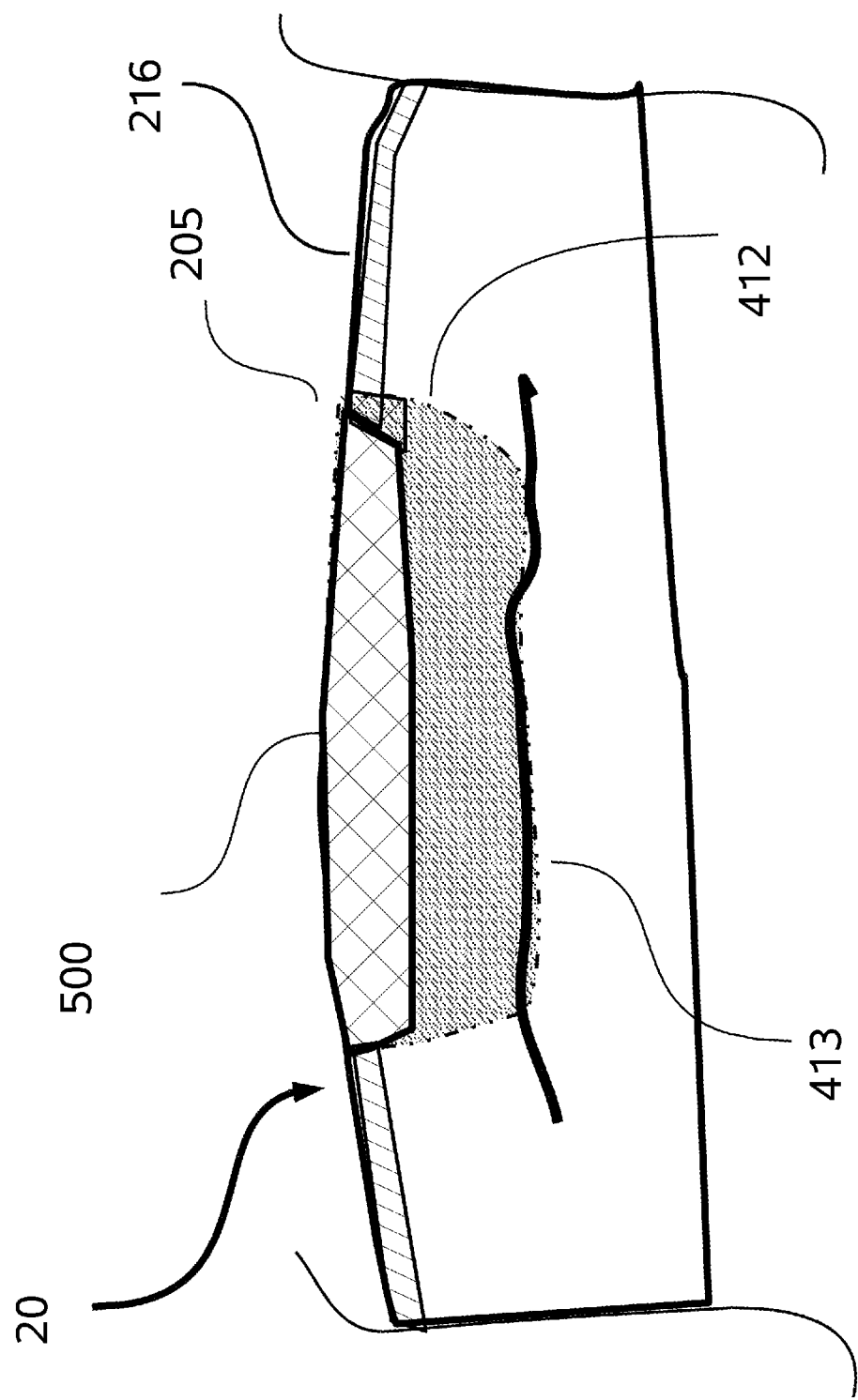
FIG. 5 is a schematic section of a patient showing the fourth step in the method.

Upon completion of the transcutaneous broadcast of energy in step 140, the surgical procedure commences with the surgical incision 500 opening to access the surgical site as illustrated in FIG. 5 (corresponding to step 150 of process 100 in FIG. 1). The surgical incision 500 is made along incision line 201.

The ultimate surgical procedure is facilitated by the ultrasonic treatment in combination with the infusion of the fluid super-hydrates the tissue, lessening the effects of tissue dehydration from exposure of the fatty and other tissue to air, as well as the prophylactic effect of the antibiotic agent.

Alternative energy sources may be used such as other acoustic waves that heat the tissue with pressure from the sound waves, and electromagnetic radiation, such as e.g. light, collimated light, laser or radio frequency energy that is used in a manner that minimizes cell damage while it disperses the antibiotic agent and fluid subcutaneously As reported in "An Additional Dose of Cefazolin for Intraoperative Prophylaxis" Jpn J Surg (1999) 29:1233-1236, by Ohge et al. it is desirable to provide a tissue level of Cefazolin of about 4 µg/ml to achieve a minimum inhibitory concentrations (MIC) for 80% (MIC.sub.80) of four bacterial species. The MICs of Cefazolin were determined for 360 isolates of methicillin-sensitive *Staphylococcus aureus* (MSSA), 204 isolates of *Klebsiella pneumoniae*, 314 isolates of *Escherichia coli*, and 30 isolates of *Streptococcus* spp. In light of these findings, Ohge et al. then pre-operatively treated patients with an intravenous bolus of 1 g of cefazolin was administered over a period of 3-5 minutes at the time of skin incision. Then, 5 ml of peripheral blood, about 3 g of subcutaneous adipose tissue, and peritoneum samples were obtained intraoperatively during and after the procedure. Ohge then discovered that this protocol resulted in a mean tissue concentration of about 10 µg/ml an hour after surgery commenced, but then dropped below 4 µg/ml after slightly more than 2 hours of surgery. During the same time period the serum concentration of Cefazolin decreased from about 80 to 40 µg/ml, and to about 10 µg/ml after about 4 hours.

Experimental Results

A prophylactic dose of the antibiotic Cefazolin was delivery to a patient by the above procedure prior to elective abdominoplasty using the Silberg Tissue Preparation Systems TM Model ME 800 (9801427) (Mettler Surgical, Anaheim, Calif.). About 250 cc of prewarmed saline containing 1 gm of Cefazolin was injected under a surgical incision line 201 that was about 5 cm long. Small sample of adipose tissue were taken during the surgical procedure to determine if the Cefazolin would remain above desired concentration reported by Ohge et al., and thus remain sufficiently high through the procedure. Further, blood serum samples were taken during the procedure to determine the potential for a longer term systemic delivery.

Figure 6:
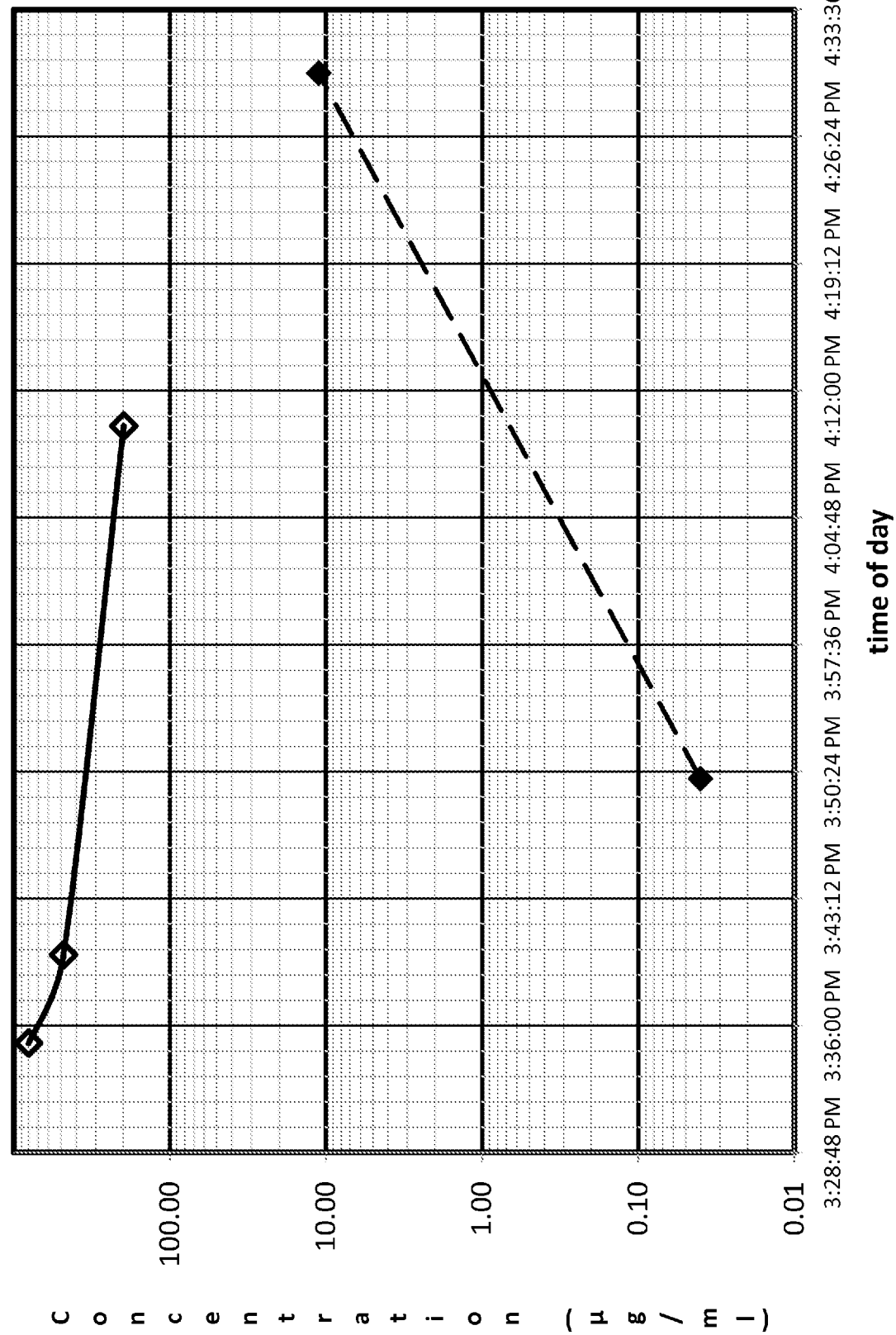
FIG. 6 is a plot comparing the time dependence of the serum and tissue concentration of a therapeutic agent.

As will now be illustrated in FIG. 6, which plots the concentration of Cefazolin over time, it has been discovered that this inventive procedure resulted in much higher adipose tissue concentration of Cefazolin at the start of surgery, for the same total dose of 1 gram as used by Ohge. The Cefazolin concentration in the adipose tissue was about 800 µg/ml at the beginning of surgery but dropped about 200 µg/ml about 50 minutes later, achieving about a 50 times greater concentration than was achieved by intravenous administration of Ohge et al.

Further, FIG. 6 also indicates that the blood serum concentrations of Cefazolin increased to about 10 µg/ml when surgery was completed about an hour later.

Notably, the above method yields antibiotic concentrations in tissue that are far beyond what could be achieved by IV delivery. It should be appreciated that the ability to achieve high tissue concentrations, such as 800 µg/ml, while likely limiting the serum concentration to less than 10 µg/ml, which less than 80× the initial tissue saturation and less than about 10× the contemporaneous tissue concentration, is a significant advantage for antibiotic agents that could be toxic at high systemic concentrations. The test data clearly demonstrates that therapeutic levels can be achieved in the target tissues with total doses that are far below the usual systemic dose levels. Even antibiotic such as Vancomycin that is relatively toxic must be brought to sufficient tissue levels to be therapeutic where it is needed. A small fraction of the usual intravenous dose could be given using this method, thus avoiding the toxic effects while treating the patient.

It should be understood that at least one species of antibiotic agents contemplated by the various embodiments of the invention includes antibiotics that are encapsulated in vesicles or are formed as nanoparticles, and more preferably those in which ultrasonic energy enhances the dispensing and delivery of the therapeutically active form of the agent.

It has further been discovered the above method also provide a means to treat patients with MRSA skin infections with antibiotics thought to be ineffective.

MRSA stands for Methicillin-resistant *Staphylococcus aureus* being a series of strains of this bacterium responsible for difficult-to-treat infections in humans being resistant to a large group of antibiotics called the beta-lactams, which include the penicillins and the cephalosporins. It may also be referred to as multiple-resistant *Staphylococcus aureus* or oxacillin-resistant *Staphylococcus aureus* (ORSA). .beta.-lactam antibiotics are a broad class of antibiotics that include penicillin derivatives, cephalosporins, monobactams, carbapenems, and .beta.-lactamase inhibitors that is, any antibiotic agent that contains a .beta.-lactam nucleus in its molecular structure, and they are generally considered the most widely-used group of antibiotics.

The inventive method was first applied prophylactically to a patent to prevent the spread of an MRSA skin infection in non-elective surgery. Surprisingly, not only was a systemic infection by MRSA prevented, but the MRSA in the surgical field of antibiotic saturated tissue visibly cleared of the infection.

Accordingly, further tests of Cefazolin with a range of different MRSA strains at concentrations well above the dose achievable by IV delivery were made to understand these finding. The Minimum inhibitory concentration (MIC) of Cefazolin with respect to these various strains is reported below in Table 1 in units are in µg/ml of Cefazolin using the broth dilution method. MIC is the lowest concentration of an antimicrobial that will inhibit the visible growth of a microorganism after overnight incubation. STA 29213 is the conventional strain of *S. aureus*, showing normal sensitivity to Cefazolin with an MIC of 0.5 µg/ml.

TABLE 1

| Organism | MIC/Cefazolin | Median MIC, µg/ml | Colony Count |
|---|---|---|---|
| MRSA 143 | 64 | 128 | 5.73E+05 |
|  | 128 |  | 4.18E+05 |
|  | 128 |  | 5.94E+05 |
| MRSA 144 | 128 | 64 | 5.12E+05 |
|  | 64 |  | 4.43E+05 |
|  | 64 |  | 5.15E+05 |
| MRSA 145 | 128 | 128 | 4.87E+05 |
|  | 128 |  | 7.50E+05 |
|  | 128 |  | 7.54E+05 |
| MRSA 146 | 64 | 64 | 5.79E+05 |
|  | 64 |  | 4.62E+05 |
|  | 128 |  | 5.68E+05 |
| MRSA 147 | 64 | 64 | 5.22E+05 |
|  | 64 |  | 3.71E+05 |
|  | 64 |  | 6.83E+05 |
| MRSA 148 | 256 | 256 | 3.45E+05 |
|  | 256 |  | 4.30E+05 |
|  | 128 |  | 4.37E+05 |
| MRSA 149 | 128 | 128 | 4.93E+05 |
|  | 128 |  | 6.97E+05 |
|  | 128 |  | 5.28E+05 |
| MRSA 150 | 512 | 512 | 4.67E+05 |
|  | 512 |  | 5.08E+05 |
|  | 512 |  | 4.92E+05 |
| MRSA 151 | 128 | 128 | 3.66E+05 |
|  | 128 |  | 4.91E+05 |
|  | 128 |  | 4.54E+05 |
| MRSA 152 | 4 | 4 | 4.03E+05 |
|  | 4 |  | 4.44E+05 |
|  | 8 |  | 5.55E+05 |
| STA 29213 | 0.5 |  | 3.02E+05 |
| MSSA | 1 |  | 5.63E+05 |
| MRSA 56 (494) | 64 | 128 | 2.04E+05 |
|  | 128 |  | 5.84E+05 |
|  | 128 |  | 6.32E+05 |
| MRSA 116 | 512 | 256 | 7.40E+05 |
|  | 256 |  | 6.32E+05 |
|  | 256 |  | 5.24E+05 |
| MRSA 142 | 256 | 256 | 4.42E+05 |
| ATCC 33591 | 256 |  | 5.26E+05 |
| MRSA | 256 |  | 5.18E+05 |
| Mu 3 | 512 | 512 | 3.52E+05 |
| MRSA | 512 |  | 4.20E+05 |
| hVISA | 512 |  | 4.42E+05 |
| Mu 50 | 256 | 256 | 5.98E+05 |
| MRSA | 256 |  | 2.68E+05 |
| VISA | 256 |  | 2.70E+05 |
| STA 25923 | 0.5 | 0.5 | 5.72E+05 |
| MSSA | 0.5 |  | 5.76E+05 |
|  | 0.5 |  | 5.82E+05 |
| STA 29213 | 0.5 | 0.5 | 4.04E+05 |

TABLE 1-continued

| Organism | MIC/Cefazolin | Median MIC, μg/ml | Colony Count |
|---|---|---|---|
| MSSA | 0.5 | | 3.94E+05 |
| | 0.5 | | 5.88E+05 |

The colony count in the last column is just a quality control measure to insure the correct innooculum.

First, it should be noted that many of these strains, being antibiotic resistant, have an MIC more than 10× the 10 μg/ml in tissue achieved by Ohge via pre-operative IV administration. However, the most resistant strain, MU 3, has an MIC of about 512 μg/ml, about 50× the dose required for normal strains. The inventive method of antibiotic administration results in much higher concentrations in tissue of at least the 800 μg/ml reported above.

It has now been discovered, inventive method provides a means to achieve the far higher therapeutic levels in the target tissues, with the resulting systemic dose but a small fraction of the amount that is customarily given by other methods, such as Ohge's.

It should also be apparent based on the above teaching that agents to reduce pain, inflammation in joints, and to infiltrate soft tissue tumors, could be administered using this technique and have the same benefit-safety ratio.

It has been discovered that the inventive procedure allows for the application of antibiotics, that would normally not be thought to be therapeutic against certain microbes, at doses at which they are therapeutic. Further, it has been discovered that despite these high local doses that yield therapeutic effects, the systemic concentration is sufficiently low so as to be likely to avoid side effects that might occur in some patients. The systemic amount is a small fraction of the amount that is customarily given by other methods while attaining far higher therapeutic levels in the target tissues.

While the invention has been described with reference to particular embodiments, it will be understood to one skilled in the art that variations and modifications may be made in form and detail without departing from the spirit and scope of the invention. Such modifications may include substituting other elements, components or structures that the invention can be practiced with modification within the scope of the following claims.

The invention claimed is:

1. A method for treating a bacterial infection in a target tissue in a subject with Cefazolin, where the bacterial infection is resistant to the antibiotic such that a minimum inhibitory concentration of the antibiotic with respect to the bacterial infection is between 64 μg/ml and 512 μg/ml, inclusive, the method comprising:
identifying the infected target tissue in the subject;
injecting subcutaneously in the subject a solution comprising the antibiotic dissolved in the solution, wherein the antibiotic is not encapsulated in vesicles;
applying an ultrasonic instrument to the subject, the ultrasonic instrument comprising a handle and a ultrasonic transducer head coupled with the handle, and wherein the ultrasonic instrument is applied to the subject by placing the ultrasonic transducer head against a skin of the subject; and
transcutaneously broadcasting ultrasonic energy from the ultrasonic transducer head while the ultrasonic transducer head is applied against the skin of the subject at a frequency within a range of 0.5 to 5 MHz for 2-5 minutes so as to disperse the dissolved antibiotic throughout the infected target tissue via microstreaming to a concentration greater than the minimum inhibitory concentration of Cefazolin with respect to the bacterial infection when sampled, thereby treating the antibiotic resistant bacterial infection.

2. The method of claim 1, wherein microstreaming comprises movement of the solution with the dissolved antibiotic in a linear direction away from a source of the ultrasonic energy.

3. The method of claim 1, wherein the infected target tissue comprises a soft tissue.

4. The method of claim 1, wherein the bacterial infection comprises a Methicillin-resistant *Staphylococcus aureus* (MRSA) infection.

5. The method of claim 1, wherein the subject comprises a human.

6. The method of claim 1, wherein the transcutaneous broadcast of ultrasonic energy from the ultrasonic transducer head superhydrates the bacterial infected target tissue with the subcutaneously injected solution comprising the antibiotic.

7. A method for treating a bacterial infection in a target tissue in a subject with Cefazolin, where the bacterial infection is resistant to the Cefazolin such that a minimum inhibitory concentration of the Cefazolin with respect to the bacterial infection is equal to or greater than 64 μg/ml and equal to or less than 512 μg/ml, the method comprising:
subcutaneously injecting, with a cannula, a solution comprising the Cefazolin dissolved in the solution to the target tissue of the subject, wherein the Cefazolin is not encapsulated in vesicles;
removing the cannula from the subject;
applying an ultrasonic instrument to the subject, the ultrasonic instrument comprising a handle and a ultrasonic transducer head coupled with the handle, and wherein the ultrasonic instrument is applied to the subject by placing the ultrasonic transducer head against a skin of the subject; and
transcutaneously broadcasting ultrasonic energy from the ultrasonic transducer head while the ultrasonic transducer head is applied against the skin of the subject at a frequency within a range of 0.5 to 5 MHz for 2-5 minutes so as to disperse the Cefazolin throughout the target tissue via microstreaming by cavitation, wherein immediately following the broadcasting of ultrasonic energy, the Cefazolin is at a concentration of at least 800 μg/ml in the target tissue when sampled, thereby treating the Cefazolin resistant bacterial infection.

8. The method of claim 7, wherein the subject comprises a human.

9. The method of claim 7, wherein the transcutaneous broadcast of ultrasonic energy from the ultrasonic transducer head superhydrates the bacterial infected target tissue with the subcutaneously injected solution comprising the Cefazolin.

10. A method for treating a Methicillin-resistant *Staphylococcus aureus* (MRSA) infection in a target tissue in a subject with Cefazolin, where the MRSA infection is resistant to the Cefazolin such that a minimum inhibitory concentration of the Cefazolin with respect to the MRSA infection is between 64 μg/ml and 512 μg/ml, inclusive, the method comprising:
creating a wound in a skin of the subject;
subcutaneously injecting through the wound, with a cannula, a solution comprising the Cefazolin dissolved in the solution to the target tissue of the subject, wherein the Cefazolin is not encapsulated in vesicles; removing the cannula from the subject;

applying an ultrasonic instrument to the subject after removing the cannula, the ultrasonic instrument comprising a handle and a ultrasonic transducer head coupled with the handle, and wherein the ultrasonic instrument is applied to the subject by placing the ultrasonic transducer head against a skin of the subject; and transcutaneously broadcasting ultrasonic energy from the ultrasonic transducer head while the ultrasonic transducer head is applied against the skin of the subject at a frequency within a range of 0.5 to 5 MHz for 2-5 minutes so as to disperse the Cefazolin throughout the target tissue via microstreaming at a concentration greater than 64 µg/ml and less than 512 µg/ml when sampled, thereby treating the Cefazolin resistant MRSA infection.

11. The method of claim 10, further comprising moving the ultrasonic transducer head over the skin of the patient during the transcutaneous broadcast of the ultrasonic energy.

12. The method of claim 10, wherein the transcutaneous broadcast of ultrasonic energy from the ultrasonic transducer head superhydrates the MRSA infected target tissue with the subcutaneously injected solution comprising the Cefazolin.

* * * * *